United States Patent [19]

Campbell

[11] Patent Number: 4,934,370
[45] Date of Patent: Jun. 19, 1990

[54] PINHOLE FOCUSED OPTICS FOR LOCATING VISUAL AXIS OF THE EYE FOR ULTRASONIC INTERIOR MEASUREMENT

[75] Inventor: Charles E. Campbell, Berkeley, Calif.

[73] Assignee: Allergan Humphrey, San Leandro, Calif.

[21] Appl. No.: 242,448

[22] Filed: Sep. 9, 1988

[51] Int. Cl.⁵ .............................................. A61B 8/00
[52] U.S. Cl. ................................................. 128/661.06
[58] Field of Search ........................... 128/661.06, 745

[56] References Cited

U.S. PATENT DOCUMENTS

| | | | |
|---|---|---|---|
| 3,371,660 | 3/1968 | Carlin | 128/661.06 |
| 4,166,695 | 9/1979 | Hill et al. | 128/745 X |
| 4,484,569 | 11/1984 | Driller et al. | 128/661.06 X |

FOREIGN PATENT DOCUMENTS 2828405  1/1979  Fed. Rep. of Germany ........................ 128/661.06

*Primary Examiner*—Francis Jaworski
*Attorney, Agent, or Firm*—Townsend and Townsend

[57] ABSTRACT

A prior art ultrasonic eye measuring device is fitted with pinhole optics. A fixation target is provided with the pinhole optics. The instrument is used to measure the dimension of the eye typically preparatory to cataract surgery. In use of the instrument, the patient has the cornea anesthetized. The patient is thereafter told to fixate on the spot of light leaking from the pinhole optics as the eye examiner brings the instrument into contact with the cornea of the eye. The point source of light approaches the eye. As it approaches, the point source increases in size. When the light source becomes sufficiently large, the fixation target becomes visible. Upon touching of the instrument to the eye, ultrasound measurement of the dimension of the eye preferably along the visual axis occurs. By the expedient of aligning the interrogating ultrasound axis to the line of sight of the fixation target, measurement of the visual axis length of the eye occurs. The appearance of the fixation target immediately before eye measurement minimizes undesired off axis measurement. In a preferred embodiment of the instrument, the conjugate image of a pinhole light source is relayed by optics through the lens of the eye. Consequently, the fixation target is not diffraction limited.

7 Claims, 1 Drawing Sheet

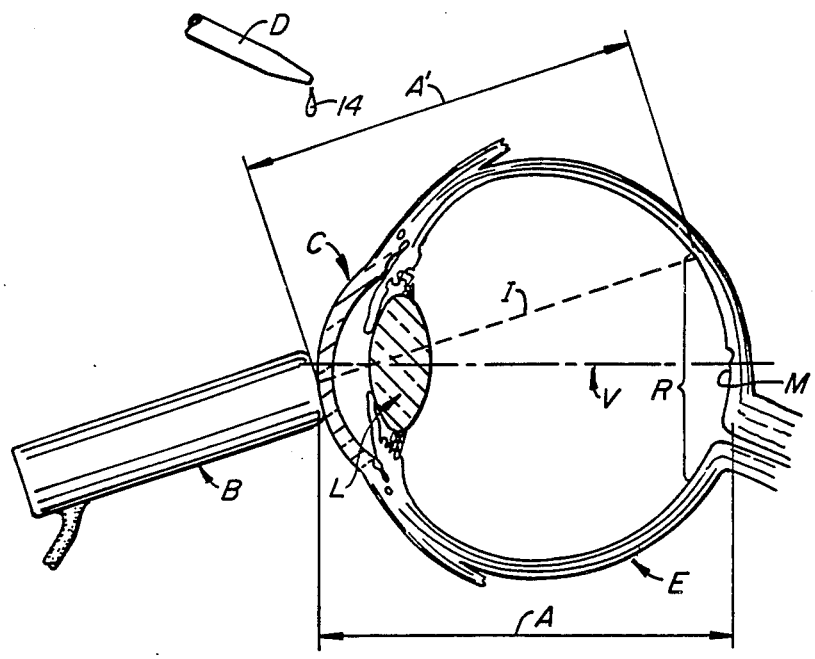
FIG._1.  PRIOR ART
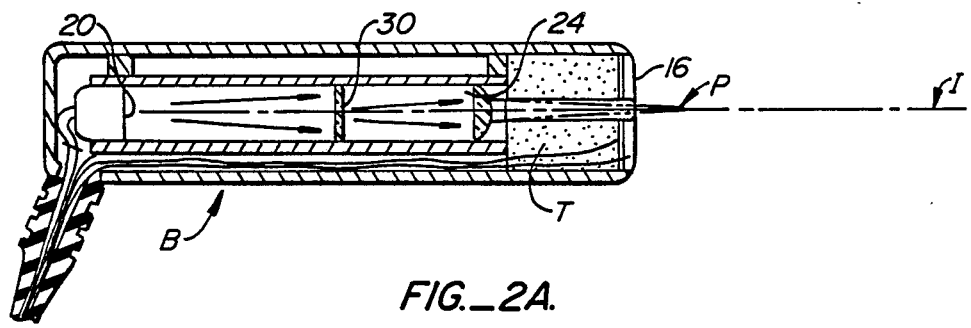
FIG._2A.
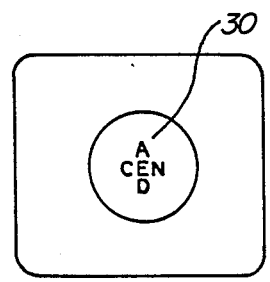
FIG._2B.
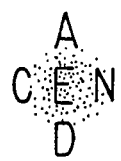
FIG._3A.  FIG._3B.

PINHOLE FOCUSED OPTICS FOR LOCATING VISUAL AXIS OF THE EYE FOR ULTRASONIC INTERIOR MEASUREMENT

BACKGROUND OF THE INVENTION

This invention relates to so-called biometer which instruments measure by ultrasound the dimension of the eye. More particularly a biometer is disclosed in which the interrogating ultrasound axis is coincident to a patient's view path to a fixation target focused through pinhole optics in the biometer.

SUMMARY OF THE PRIOR ART

So-called biometers for the ultrasonic measurement of the internal dimensions of the eye are known. One such instrument is sold by Allergan Humphrey, a division of SmithKline Beckman of San Leandro, Calif. under the designation Ultrasonic Biometer Model 820.

Such an instrument is utilized typically on elderly patients in preparation for cataract surgery. It will therefore be understood that the subjects or patients on whom these instruments are utilized commonly have diminished visual perception. These patients are further usually hindered by the normal infirmities of age. Additionally, and since the patients are candidates for eye surgery, they are understandably apprehensive.

The operation of such conventional biometers is easy to understand. The instrument includes a piezoelectric device for the generation of interrogating ultrasound and for the reception of the telltale reflecting sound. The piezoelectric device transmits the interrogating ultrasound to the eye and receives reflected sound from the eye. In the above Allergan Humphrey Biometer Model 820. the biometer upon touching the cornea of the eye immediately generates interrogating ultrasound and receives telltale reflected sound. Timing information extracted from the returning telltale ultrasound generates measurement. Since the operative mechanics of biometers are known, they will not be further discussed here.

The utility of such instruments can be easily understood. The dimension of the eye is obtained by the biometer. The dimension of the cornea is typically measured with the keratometer. Combining these two dimensions, both the location and power of a transplanted eye lens can be selected. With this information, removal of the natural eye lens with the cataract and substitution of the transplant lens can lead to improved vision.

Unfortunately, the eye is a spheroid with elliptical section. Consequently, many different measurements along many different chords of the eye are possible. Unfortunately, the measurement along the visual axis of the eye to the macula lutea is the required measurement for proper prediction of lens placement and lens power. This particular axis cannot be located merely from the dimension of the eye. Consequently patient fixation is required to assist in location of this visual axis.

The prior art has attempted to provide fixation targets for biometer testing. Usually such fixation targets have included an optical fiber. The fiber is placed through the interrogating surface of the biometer. The fiber emits light through the transparent portion of the interrogating surface.

Such fiber optics with biometers are moved from a position away from the eye to a position touching the eye. Initially, the patient sees a light out in space upon which fixation is possible. Unfortunately, this perception of the light spot only occurs as the instrument approaches the patient's eye.

When the biometer makes measuring ultrasound contact with the eye, fixation on such optical fiber is lost. What formerly was a spot on which fixation could occur becomes a large blur of amorphous shape. This large blur of amorphous shape—seen typically through a cataract by the patient—causes lost of fixation. Consequently, corresponding loss of the required fixation for proper measurement of the visual axis of the patient can result. This loss of fixation is typical among aging patients having defective eyesight apprehensive about possible and probable eye surgery.

Alternate methods for the preservation of fixation during measurement of the visual axis are largely unsatisfactory. For example, techniques exist for utilizing the fixation of the opposite or "fallow" eye for fixation. Unfortunately, in the elderly, such fixation can be inaccurate. This is especially true in the usual case where the vision of at least one of the eyes has been seriously degraded for an appreciable period prior to the required examination and measurement.

In short, no reliable method for preserving fixation during the measurement of eye dimension by a biometer has been proposed.

It is known to have devices for projecting through pinhole optics acuity targets to the eye. Such devices do not contact the cornea of the eye. They are specialized for projecting through or around the cataracts an image through pinhole optics. This image is used on a recognition basis to make sure that the retina of the candidate for cataract surgery is functional. By determining function of the retina, needless lens transplant operations can be avoided where other eye dysfunctions make improved vision not possible.

SUMMARY OF THE INVENTION

A prior art ultrasonic eye measuring device is fitted with pinhole optics. A fixation target is provided with the pinhole optics. The instrument is used to measure the dimension of the eye typically preparatory to cataract surgery. In use of the instrument, the patient has the cornea anesthetized. The patient is thereafter told to fixate on the spot of light leaking from the pinhole optics as the eye examiner brings the instrument into contact with the cornea of the eye. The point source of light approaches the eye. As it approaches, the point source increases in size. When the light source becomes sufficiently large, the fixation target becomes visible. Upon touching of the instrument to the eye, ultrasound measurement of the dimension of the eye preferably along the visual axis occurs. By the expedient of aligning the interrogating ultrasound axis to the line of sight of the fixation target, measurement of the visual axis length of the eye occurs. The appearance of the fixation target immediately before eye measurement minimizes undesired off axis measurement. In a preferred embodiment of the instrument, the conjugate image of a pinhole light source is relayed by optics through the lens of the eye. Consequently, the fixation target is not diffraction limited.

OTHER OBJECTS, FEATURES AND ADVANTAGES

An object of this invention is to disclose a biometer with a built in fixation target broadcast through pinhole optics on the interrogating acoustical surface of the biometer. Accordingly, a pinhole light source has a conjugate image of the light source focused through biometer mounted optics to the eye. Between the light source and the conjugate image of the light source, there is placed a transparent acuity target. The axis from the pinhole light source through the acuity target to the conjugate image of the pinhole light source is made coincident to the axis of acoustical interrogation. The conjugate image of the pinhole light source is positioned slightly in front of the biometer to register with the lens of the eye immediately before interrogating acoustical contact.

An advantage of this invention is that just before eye dimension is measured, the acuity target appears to the patient. This appearance causes patient fixation with resultant alignment of the visual axis of the eye to the interrogating acoustical axis of the biometer. Consequently, accurate dimension of the visual axis of the eye is obtained.

An advantage of the use of the conjugate image of the pinhole light source in the required pinhole optics is that the fixation target is not diffraction limited by a conventional pinhole Consequently, the disclosed instrument is capable of projecting all fixation targets without appreciable size limitation due to the effects of diffraction.

It is an additional advantage to disclose a process of eye measurement utilizing the disclosed instrument. Simply stated, it has been found that the appearance of the acuity target immediately before visual axis measurement causes patient concentration on the fixation target. In the case of an elderly and infirm patient having otherwise defective vision, this concentration on fixation maximizes the possibility of obtaining accurate measurement.

BRIEF DESCRIPTION OF THE DRAWINGS

Other objects, features and advantages of this invention will be more apparent after referring to the following specification and drawings in which:

FIG. 1 is a side elevation section of an eye measured by a prior art biometer illustrating the commonly experienced misalignment of the instrument in determining the dimension of the visual axis the misalignment here being somewhat exaggerated for purposes of understanding;

FIG. 2 is a side elevation section of the instrument of this invention illustrating the improvement of the pinhole optic fixation target added in combination with the instrument, the section here illustrating the coincident of the interrogating acoustical axis to the line of sight to the fixation target: and.

FIGS. 3A and 3B are a cartoon series of a patient's eye view of the fixation target with FIG. 3A illustrating the spot of light initially seen by the patient as the instrument approaches the patient's eye and FIG. 3B illustrating the suddenly appearing fixation target in the form of the letter "E," it being understood that this target is seen instants before measurement is taken along the visual axis of the eye.

Referring to FIG. 1, a biometer B shown connected to conventional prior art acoustical circuitry and printout mechanisms (not shown) is shown addressed to the cornea C of an eye E. The eye, shown in cross-section, includes a lens 1 and a visual axis V. The visual axis V is a line of sight through lens L to the macula M on the retina R of the eye.

It will be remembered that before the measurement is taken, an eye dropper D typically places a droplet 14 of anesthetic onto the cornea C.

A biometer B is shown addressed to the cornea C. Typically, the biometer typically has coaxially of the cylindrical shape of the instrument an interrogating axis I.

It can be seen that the distance from the cornea C to the macula M is equal to the interval A.

In the prior art of FIG. 1, the interrogating axis I can measure a second and different distance A'. It is the measurement of the second and different distance A' that causes the error.

Having set forth the typically erroneous measurement of the prior art, the improvement of this invention can be set forth with respect to FIG. 2.

Referring to FIG. 2A, a section of the biometer B is illustrated. Typically, the instrument is cylindrical. It includes an ultrasound transducer T attached to an acoustical interrogating surface 16. Transducer T functions to first transmit interrogating acoustical ultrasound and receive reflecting telltale ultrasound from the eye. By conventional time gating of the reflecting telltale ultrasound, the dimension of the eye E shown in FIG. 1 can be obtained.

The improvement of FIG. 2 is relatively easy to understand. A pinhole light source 20, preferably a light emitting diode, emits light to a relay lens 24. Relay lens 24 focuses a conjugate image of the pinhole light source 20 to a conjugate pinhole P.

Conjugate pinhole P is relayed through a transparent volume of small dimension in the center portion of both the piezoelectric device T and the interrogating surface 16. The conjugate pinhole P is positioned to be slightly in front of interrogating surface 16. It registers with the eye lens upon biometer contact with the eye and acoustical interrogation.

Between the light source 20 and the pinhole P there is placed a transparent target 30. Transparent target in the form of a central letter E. this central letter E being surrounded here by other letters (see FIG. 3B). These letters include the upper letter "A," the lower letter "D," the left letter "C," and the right letter "N." Fixation target 30 has its image projected through the pinhole optics P.

It will be understood that placement of the target 30 can likewise occur at virtually any other location in the biometer between the light emitting diode 20 and the pinhole P.

It is further to be understood that the view to the fixation target 30 at the letter "E" and the interrogating acoustical axis I of the biometer are coincident. It is this coincidence which maximizes fixation of the patient along the interrogating axis I of the instrument.

Having set forth the simple construction, the operation of this instrument can be described. It will be remembered that the instrument is used on an elderly patient in preparation for cataract surgery. The patient usually has the normal infirmities of age compounded by diminished visual perception. At the same time it is the normal case that the patient has an understandable amount of anxiety about the possibility of cataract surgery.

As illustrated in FIG. 1, the cornea of the eye of the patient is first anesthetized. Thereafter, the patient is told to fixate on the approaching biometer. In such fixation, light leaking from the pinhole P will be a fixation target. This light leakage will be similar to prior art instruments having an optical fiber. (See the view of FIG. 3A.)

Here, however, because of the pinhole optics P and the target 30, the patient is given an entirely different expectancy. The patient is asked to cooperate with the examiner and inform the examiner when the center portion of the fixation target is first seen. This is the letter "E".

As the biometer approaches the cornea of the patient, it initially appears as a point source of light. This point source gradually expands. As the point source of light gradually expands, it becomes large enough for the patient to fixate on the contained target. Assuming that the instrument is properly aligned, the letter "E" will first become visible. Thereafter, the surrounding letters will come into view.

The patient is asked to fixate on the letter "E." As the shape of the letters begins to appear, the normal visual reflexes of the patient instantly pan the eye to align the macula M with the line of sight to the letter E.

It is important to note that the perception of the letter "E" through the pinhole optics P occurs immediately before the interrogating surface 16 contacts the cornea. When the interrogating surface 16 contacts the cornea C, the eye E of the patient will have a maximized possibility of aligning the visual axis V coincident to the interrogating axis I. Since the prior art instrument herein described takes the optical measurement upon first contact with the cornea C, the measurement will be taken immediately after the patient has fixated on the acuity target, here in the form of the letter "E".

It should be noted that even where the lens L of the eye is obscured by a cataract, the pinhole optics P have the maximum possibility of seeing through the obscured lens L. Further, and because cataracts cloud some portions of a lens, and leave other portions of eye lens transparent, it is possible to address the instrument to the eye along the transparent portions of the lens L to obtain the measurement.

It is stressed that it is the cooperative function of the device to distract the patient with the natural reflex of fixation to overcome diminished visual perception, age, and usual presurgical apprehension.

I have here illustrated the projection of a pinhole light source for the preferred embodiment of this instrument. A conventional pinhole could be used. It will be understood, however, that a conventional pinhole will introduce diffraction effects. These effects will limit the acuity and hence the size of the letters that can be used with the fixation target. Thus, the projection of the conjugate image of the pinhole light source is definitely preferred.

I claim:

1. In a biometer for the ultrasonic measurement of the dimension of the eye said biometer including an eye contact surface for touching the surface of an anesthetized eye, a piezoelectric device for generating ultrasound for interrogating the dimension of said eye along an interrogating axis with respect to said piezoelectric device and receiving reflected telltale ultrasound from said eye having time interval spacing reflecting the dimension of said eye, means mounting said piezoelectric device in acoustical communication to said eye contact surface for transmitting and receiving said ultrasound, the improvement to said biometer comprising:
   a transparent aperture in said eye contact surface;
   a light source interior of said biometer for transmitting light;
   means for addressing a pinhole optic aperture to the eye;
   an acuity target between said light source and pinhole optic aperture for projection through said transparent aperture to the eye whereby an eye immediately proximate to said optic pinhole aperture can see said acuity target,
   means mounting said acuity target relative to said pinhole, aperture so that the line of sight between said pinhole optic aperture and acuity target is coincident to the interrogating axis of said piezoelectric device.

2. The invention of claim 1 and including wherein:
   said light source is a pinhole light source; and
   said means for addressing a pinhole optic aperture to the eye includes a relay lens for focusing an image of said pinhole optics to the lens of the eye.

3. The invention of claim 2 and wherein said acuity target is spaced apart from said relay lens.

4. The invention of claim 1 and wherein said light source is a light emitting diode.

5. A biometer for the ultrasonic measurement of the dimension of the eye, said biometer comprising:
   an eye contact surface for touching the surface of the cornea of an anesthetized eye;
   a piezoelectric device for generating ultrasound for interrogating the dimension of said eye and receiving reflected telltale ultrasound from the eye having time interval spacing reflecting the dimension of said eye, said piezoelectric device aligned for acoustical interrogation along an axis with respect to said piezoelectric device:
   a transparent aperture in said piezoelectric device;
   a light source interior of said biometer for transmitting light;
   means for addressing a pinhole optic aperture to the eye through said transparent aperture;
   an acuity target between said pinhole optic aperture and said light source for imparting through said pinhole optic aperture an image of an acuity target whereby an eye immediately approximate to said pinhole optic aperture can see said acuity target.

6. The invention of claim 5 and wherein said light source is a pinhole light source; and,
   said means for addressing a pinhole optic aperture include a relay lens for relaying a conjugate image of said pinhole light source to the eye lens of a patient.

7. In the process of measuring the dimension of an eye with the piezoelectric device including the steps of:
   providing a piezoelectric device;
   gradually bring said piezoelectric device into contact with the cornea of an anesthetized eye;
   emitting interrogating ultrasound to said eye after contact with said eye; and
   receiving telltale reflected sound from said eye having time spacing reflecting the dimension of said eye, the improvement comprising:
   providing a pinhole optic aperture in said piezoelectric device;
   providing a light source for emitting light to said pinhole optic aperture;
   placing an acuity target between said light source and pinhole optic aperture with the visual axis to said pinhole optic aperture being coincident to the interrogating axis of said piezoelectric device;
   moving said biometer into contact with a patient's eye from a position of fixation on light from said pinhole to a proximity wherein said acuity target can be visible through said pinhole optic aperture; and,
   taking the dimension of said eye with said biometer upon contact with said eye.

* * * * *